United States Patent
Huang et al.

(10) Patent No.: US 8,697,469 B2
(45) Date of Patent: Apr. 15, 2014

(54) PROTEIN TRANSISTOR DEVICE

(71) Applicant: National Chiao Tung University, Hsinchu (TW)

(72) Inventors: Gue-Wha Huang, Jhunan Township, Miaoli County (TW); Meng-Yen Hung, Jhunan Township, Miaoli County (TW); Yu-Shiun Chen, Toucheng Township, Yilan County (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 13/691,547

(22) Filed: Nov. 30, 2012

(65) Prior Publication Data
US 2014/0048776 A1 Feb. 20, 2014

(30) Foreign Application Priority Data
Aug. 17, 2012 (TW) .............................. 101129877 A

(51) Int. Cl.
*H01L 21/00* (2006.01)
(52) U.S. Cl.
USPC ........... 438/49; 438/1; 287/414; 287/E51.023
(58) Field of Classification Search
CPC .... H01L 29/16; H01L 29/0665; H01I 29/207; G01N 21/658
USPC ................ 438/1; 257/E51.023; 977/937, 958
See application file for complete search history.

(56) References Cited

U.S. PATENT DOCUMENTS

| | | | |
|---|---|---|---|
| 6,482,639 B2 * | 11/2002 | Snow et al. | ................. 435/287.2 |
| 2003/0096113 A1 * | 5/2003 | Jacobson et al. | ............... 428/379 |
| 2005/0106804 A1 * | 5/2005 | Aviram | ......................... 438/233 |
| 2006/0052947 A1 | 3/2006 | Hu | |
| 2011/0033940 A1 | 2/2011 | Mirkin et al. | |
| 2011/0171749 A1 | 7/2011 | Alocilja et al. | |
| 2011/0281288 A1 | 11/2011 | Chen et al. | |
| 2012/0045748 A1 | 2/2012 | Willson | |
| 2012/0050732 A1 | 3/2012 | Lu | |

OTHER PUBLICATIONS

Yu-Shiun Chen et al., "A protein transistor made of an antibody molecule and two gold nanoparticles", Nature Nanotechnology;Supplemtary Information Feb. 26, 2012, 17 pages.
Yu-Shiun Chen et al., "A mother platform made of protein transistor for the application of drug screening, personal genome sequencing, and ultra-sensitive biosensing device", National Chiao Tung University, 2012 Joint Presentation on Biomedical Technology Achievement, Jun. 8, 2012, 15 pages.

(Continued)

*Primary Examiner* — Caridad Everhart
(74) *Attorney, Agent, or Firm* — Muncy, Geissler, Olds & Lowe, P.C.

(57) ABSTRACT

The present invention discloses a protein transistor device, wherein an antibody molecule (antibody-antigen) is bonded to at least two gold nanoparticles in a high reproducible self-assembly way to form molecular junctions, and wherein the two gold nanoparticles are respectively joined to a drain and a source. The protein transistor device can be controlled to regulate current via applying a bias to the gate. The conformational change of the protein molecule will cause the variation of the charge transport characteristics of the protein transistor device. The protein transistor device can be further controlled by different optical fields via conjugating a quantum dot to the molecular junctions. Therefore, the present invention has diversified applications.

16 Claims, 3 Drawing Sheets

(56) References Cited

OTHER PUBLICATIONS

Steve Huang, "Application of Bio-Nano interface in Molecular Electronics and Nanofabrication", Laboratory of Molecular Electronics and Biocomputer, Oct. 2, 2012, 20 pages.

Mao-Shivan Chen, "Reveal a drop of blood! Life of birth inspection disease can predict", on cnYES News, Mar. 23, 2012, 2 page.

Chao-Lun Chiang, "Unique! It is not a dream of customized medicine", on Yahoo! Kimo News, Mar. 23, 2012, 1 page.

The Voice of NCTU Alumni, May 15, 2012, 1 page.

Ming-Yang, Lee, "Antibody transform transistor", Scientific American, May 28, 2012, 1 page.

Carmeli, I., Frolov, L., Carmeli, C. & Richter, S., "Photovoltaic activity of Photosystem I-Based Self-Assembled Monolayer", J. Am. Chem. Soc. vol. 129, No. 41, pp. 12352-12353 (May 15, 2007).

Rupa Das, Patrick J. Kiley, Michael Segal, Julie Norville, A. Amy Yu, Leyu Wang, Scott A. Trammell, L. Evan Reddick, Rajay Kumar, Francesco Stellacci, Nikolai Lebedev, Joel Schnur, Barry D. Bruce, Shuguang Zhang, and Marc Baldo, "Integration of Photosynthetic Protein Molecular Complexes in Solid-State Electronic Devices", Nano Letters vol. 4, No. 6 pp. 1079-1083 (2004).

Giuseppe Maruccio, Adriana Biasco, Paolo Visconti, Alessandro Bramanti, Pier Paolo Pompa, Franco Calabi, Roberto Cingolani, Ross Rinaldi, Stefano Corni, Rosa Di Felice, Elisa Molinari, Martin P. Verbeet, and Gerard W. Canters, "Towards Protein Field-Effect Transistors: Report and Model of a Prototype", Advanced Materials 17, No. 7, Apr. 4, pp. 816-822 (2005).

Giuseppe Maruccio, Pasquale Marzo, Roman Krahne, Adriana Passaseo, Roberto Cingolani, and Ross Rinaldi, "Protein Conduction and Negative Differential Resistance in Large-Scale Nanojunction Arrays", Small 3, No .7, pp. 1184-1188 (2007).

Mentovich, E. D., Belgorodsky, B., Kalifa, I., Cohen, H. & Richter, S., "Large-Scale Fabrication of 4-nm-Channel Vertical Protein-Based Ambipolar Transistors", Nano Letters, vol. 9, No. 4, pp. 1296-1300 (2009).

\* cited by examiner

PROTEIN TRANSISTOR DEVICE

BACKGROUND OF THE INVENTION

1. Field of the Invention

The present invention relates to a protein transistor device, particularly to a protein transistor device having molecular junctions fabricated via bonding an IgG molecule to gold nanoparticles in a self-assembly way.

2. Description of the Related Art

As early as 1974, Avi Aviram and Mark Ratner had proposed that a single organic molecule can be used to construct a simple electronic element functioning as a rectifier, which has been regarded as the origin of the molecular electronics. Recently, some research teams have explored biomolecules applicable to molecular electronics and used them to explain some evolution phenomena occurring in the past millions of years, such as electron transport, photochemical conversion, and molecular recognition.

It is very difficult to control the connection of biomolecules and structures in the molecular scale. Although many methods have been proposed to bond biomolecules to structures, all of them lack reproducibility. Besides, the biomolecular electronics has another problem—performance deterioration. In the technologies applying a single molecule to a nanoelectronic element, electron migration and bond breaking are the most common methods to form covalent bonds between molecules and electrodes. However, the abovementioned methods imply high uncertainty and instability in bonding. How to form stable current is another problem after the bonding is made thereby. Therefore, the current technologies are unlikely to fabricate required molecular structure in a large scale. Besides, the bonding of molecules and structures may change molecular structure and affect the function of the molecular-scale elements.

Accordingly, the present invention proposes a protein transistor device to overcome the abovementioned problems.

SUMMARY OF THE INVENTION

The primary objective of the present invention is to provide a protein transistor device, wherein the IgG (immunoglobulin G) molecule is bonded to gold nanoparticles in an antibody-antigen self-assembly way, which can generate stable bonding for different molecules in a high reproducibility.

Another objective of the present invention is to provide a protein transistor device, wherein a quantum dot is conjugated to a molecular junction, whereby the protein transistor device can be gated with different optical fields, and whereby is diversified the application of the protein transistor device.

A further objective of the present invention is to provide a protein transistor device, which incorporates biological functions into the nanoelectronic elements and would push the applications of the next-generation nanoelectronics in the many fields, such as biology, medical diagnosis, medicine and quarantine.

To achieve the abovementioned objectives, the present invention proposes a protein transistor device, which comprises a transistor and at least two gold nanoparticles, wherein the transistor has a drain, a source and a gate, and wherein a nanochannel is formed between the drain and the source, and wherein two gold nanoparticles are respectively arranged on the drain and the source, and wherein a first antibody molecule is bonded to two gold nanoparticles through the nanochannel in a self-assembly way to form molecular junctions.

The present invention also proposes a method for fabricating protein molecular junctions, which comprises steps: respectively bonding at least two gold nanoparticles, which function as interfaces stabilizing the molecules and the electrodes, to two electrodes; applying a bias to the two electrodes to enable a first antibody molecule to bond to at least two gold nanoparticles in a self-assembly way and form molecular junctions.

Below, embodiments are described in detail to make easily understood the objectives, technical contents, characteristics and accomplishments of the present invention.

DETAILED DESCRIPTION OF THE INVENTION

Figure 1:
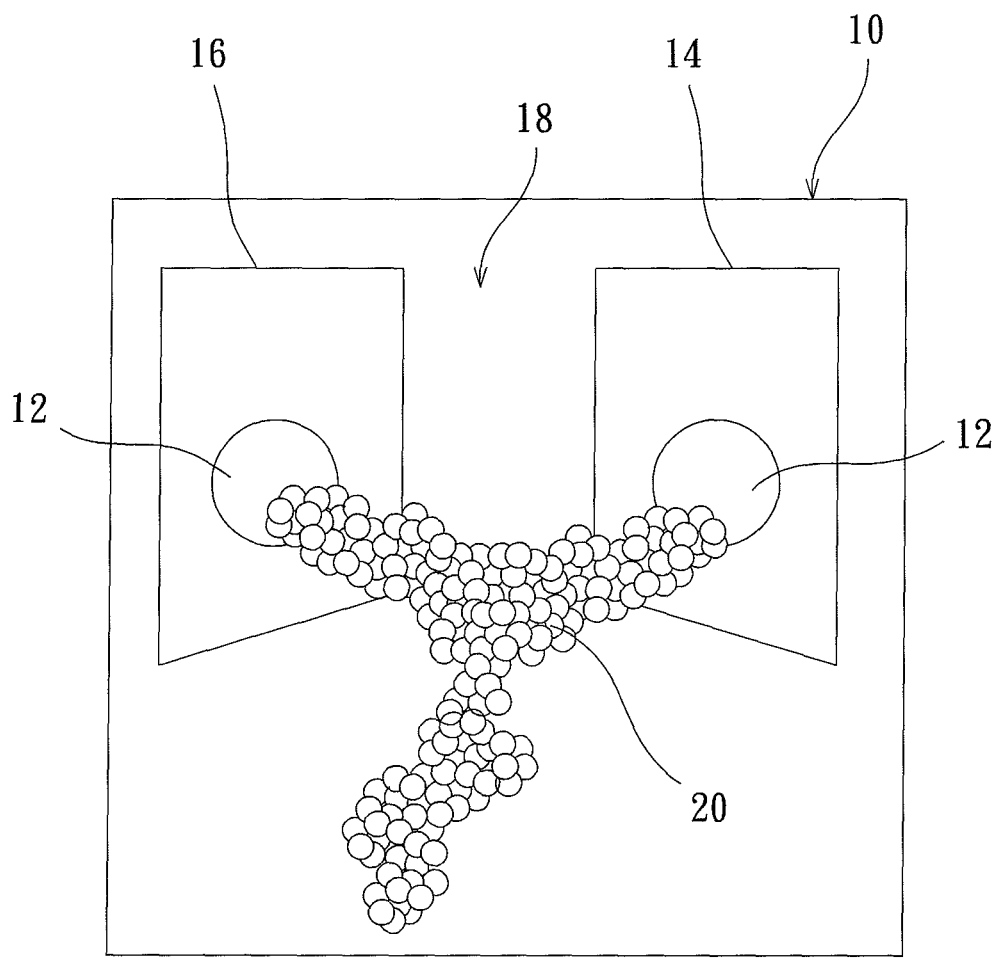
FIG. 1 schematically shows the structure of a protein transistor device according to one embodiment of the present invention.

The present invention proposes a novel protein transistor device intended to offer a versatile platform for investigations of single-molecule-based biological functions, which may leads to large-scale manufacture of molecular electronic circuits. Refer to FIG. 1 schematically showing the structure of a protein transistor device according to one embodiment of the present invention. The protein transistor device of the present invention comprises a transistor 10 and at least two gold nanoparticles 12. The transistor 10 has a drain 14, a source 16 and a gate (not shown in FIG. 1). A nanochannel 18 having a width of 5-15 nm is fabricated with AFM (Atomic Force Microscope) and an electron beam lithographic technology. The nanochannel 18 is between the drain 14 and the source 16. Two gold nanoparticles 12 are respectively bonded to the drain 14 and the source 16. The gold nanoparticle 12 can function as an interface stabilizing the bonding of the molecule and the electrode. A high-reproducibility and high-stability first antibody molecule 20, which is an IgG (immunoglobulin G) molecule in this embodiment, is bonded to the two gold nanoparticles 12 through the nanochannel 18 in a self-assembly way, whereby to form molecular junctions. The first antibody molecule 20 has a Y shape. Two arms of the Y shape are respectively bonded to the surfaces of the two gold nanoparticles 12. The gold nanoparticle 12 has a diameter of 5 nm. Applying a bias to the gate can control the transistor 10 to regulate current and charge transport. Varying the bias can change the characteristics of the charge transport of the protein transistor device. The molecular junction can stabilize the bonding for different molecules.

Figure 2:
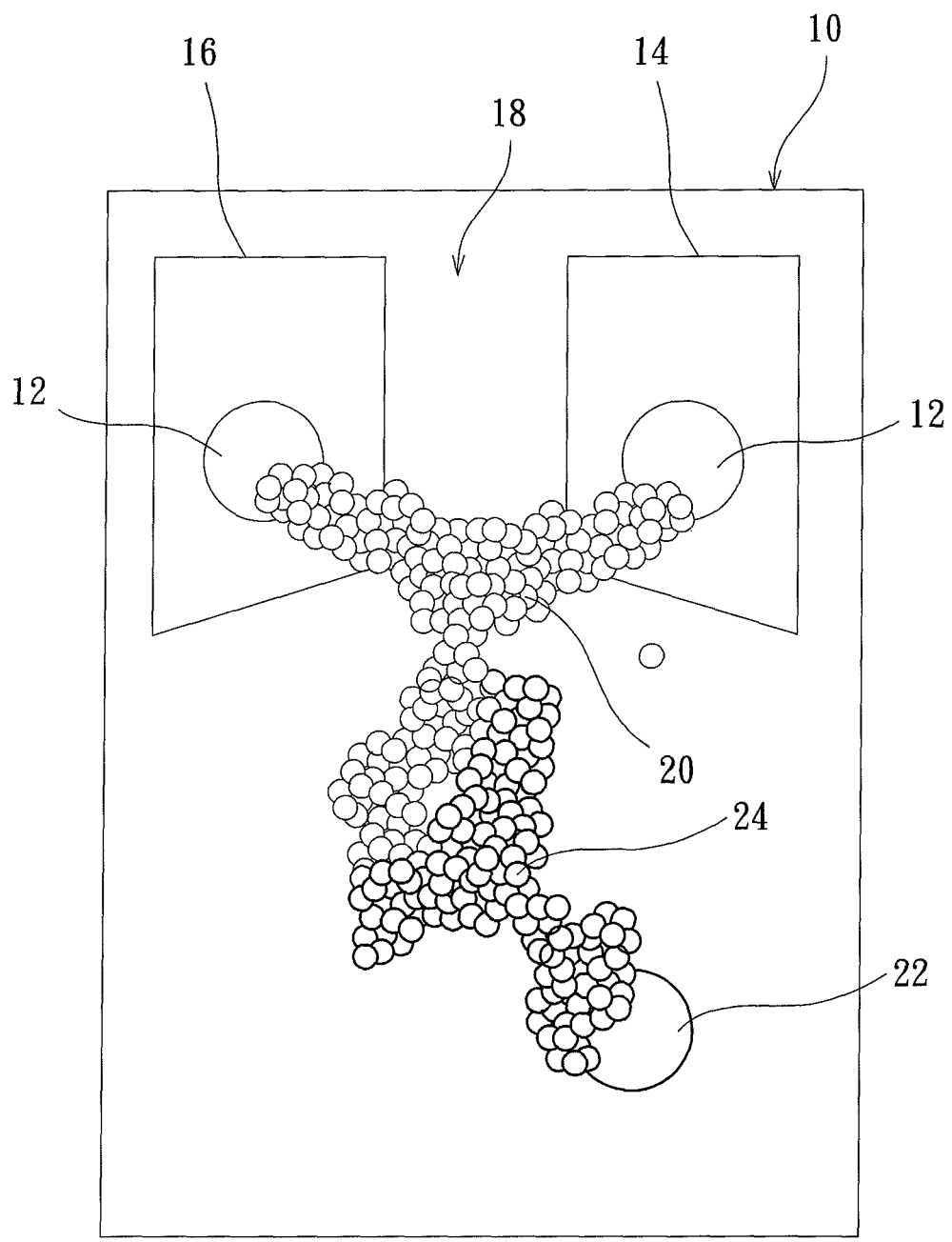
FIG. 2 schematically shows that a quantum dot is conjugated to a protein transistor device according to one embodiment of the present invention.

Refer to FIG. 2 schematically showing that a quantum dot is conjugated to a protein transistor device according to one embodiment of the present invention. In one embodiment, a quantum dot 22 is conjugated to a second antibody molecule 24, and the second antibody molecule 24 is bonded to the molecular junctions, such as the stalk of the Y shape. In this embodiment, the second antibody molecule 24 is a high-reproducibility and high-stability IgG (immunoglobulin G) molecule; the quantum dot is made of cadmium selenide. In addition to applying a bias to the gate, the transistor can be turned on or off via applying an optical field to the quantum dot 22. Therefore is diversified the application of the protein transistor device.

Figure 3:
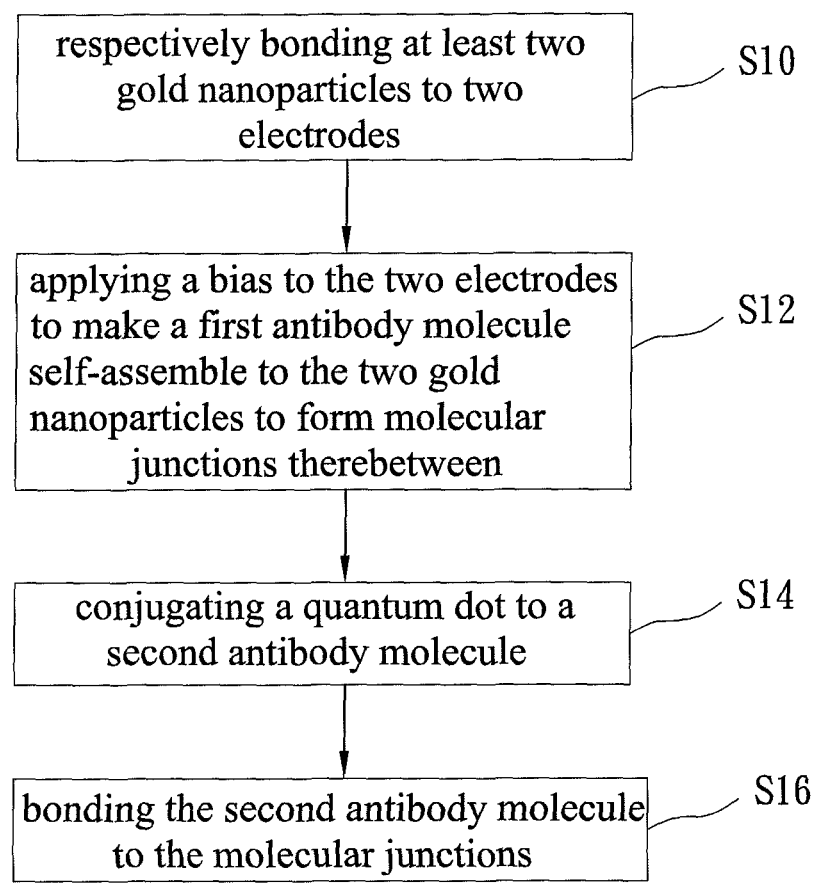
FIG. 3 is a flowchart of a method for fabricating a protein transistor device according to one embodiment of the present invention.

Refer to FIG. 2 and FIG. 3. FIG. 3 is a flowchart of a method for fabricating a protein transistor device to integrate a biological function and a transistor according to one embodiment of the present invention. In Step S10, respectively bond at least two gold nanoparticles 12 to two electrodes. In one embodiment, the two electrodes are respectively a drain 14 and a source 16, and a nanochannel having a width of 5-15 nm is formed between the drain 14 and the source 16. The gold nanoparticles 12 can function as an interface stabilizing the molecule and electrode during bonding. In Step S12, apply a bias to the drain 14 and the source 16 (apply a bias to the gate beforehand) to enable a first antibody molecule 20 to bond to the two gold nanoparticles 12 in a self-assembly way, whereby are formed molecular junctions therebetween.

In one embodiment, the first antibody molecule 20 is an IgG (immunoglobulin G) molecule. The first antibody molecule 20 and the gold nanoparticles 12 can enhance the detection sensitivity in biotest and instant inspection. The two gold nanoparticles 12 function as the contact media. Applying a bias enables the first antibody molecule 20 to bond to the two gold nanoparticles 12 in a self-assembly way, which is a novel self-assembly method having high reproducibility. Thereafter, the current can be controlled via only applying a bias to the gate. In fabricating a large size electronic circuit, the required quantity of gold nanoparticles 12 is bonded to the electrodes, and let the first antibody molecules 20 self-assemble to the gold nanoparticles 12.

The application of the protein transistor device can be further diversified via the following steps. In Step S14, conjugate a quantum dot 22 made of cadmium selenide to a second antibody molecule 24. In one embodiment, the second antibody molecule 24 is an IgG molecule. In Step S16, bond the second antibody molecule 24 to the molecular junctions. As the first antibody molecule 20 and the second antibody molecule 24 are identical antibodies or antigens, they can bond to each other stably. Thereby, the transistor can be turned on or off via applying different optical fields. Other antibody molecules having different functions can also be bonded to the molecular junctions to meet requirements of the market.

In conclusion, the present invention integrates a biological function and a nanoelectronic element to form a high-reproducibility and high-stability protein transistor device, which will push the molecular electronics toward the next-generation nanoelectronics and may apply to the fields of biology, medical diagnosis, medicine and quarantine. The present invention can also apply to various biotests, such as glucose tests, pregnancy tests, blood tests, virus tests, and DNA tests. The present invention may further be used to monitor the environmental poisons or fabricate artificial noses. Therefore, the present invention is very useful has very high market potential.

The embodiments described above are only to exemplify the present invention but not to limit the scope of the present invention. Any equivalent modification or variation according to the characteristic or spirit of the present invention is to be also included within the scope of the present invention.

What is claimed is:

1. A protein transistor device comprising
a transistor having a drain, a source and a gate, wherein a nanochannel is formed between said drain and said source;
at least two gold nanoparticles respectively installed in said drain and said source, wherein a first antibody molecule is bonded to said two gold nanoparticles through said nanochannel in a self-assembly way to form molecular junctions; and
a quantum dot conjugated to a second antibody molecule, wherein said second antibody molecule is bonded to said molecular junctions.

2. The protein transistor device according to claim 1, wherein current regulation and charge transport of said transistor are controlled via applying a bias to said gate.

3. The protein transistor device according to claim 1, wherein said quantum dot is made of cadmium selenide.

4. The protein transistor device according to claim 1, wherein said transistor is turned on or off via applying an optical field to said quantum dot.

5. The protein transistor device according to claim 1, wherein said second antibody molecule is an IgG (immunoglobulin G) molecule.

6. The protein transistor device according to claim 1, wherein said first antibody molecule is an IgG (immunoglobulin G) molecule.

7. The protein transistor device according to claim 1, wherein said nanochannel has a width of 5-15 nm.

8. The protein transistor device according to claim 1, wherein said gold nanoparticle has a diameter of 5 nm.

9. A method for fabricating protein molecular junctions, comprising steps:
bonding at least two gold nanoparticles respectively to two electrodes;
applying a bias to said two electrodes to make a first antibody molecule self-assemble to said two gold nanoparticles to form molecular junctions; and
conjugating a quantum dot to a second antibody molecule and bonding said second antibody molecule to said molecular junctions after said molecular junctions have been formed.

10. The method for fabricating protein molecular junctions according to claim 9, wherein said first antibody molecule is an IgG (immunoglobulin G) molecule.

11. The method for fabricating protein molecular junctions according to claim 9, wherein said quantum dot is made of cadmium selenide.

12. The method for fabricating protein molecular junctions according to claim 9, wherein said second antibody molecule is an IgG (immunoglobulin G) molecule.

13. The method for fabricating protein molecular junctions according to claim 9, wherein said bias is applied to a gate beforehand to supply said two electrodes with said bias, and wherein said two electrodes are respectively a drain and a source, and wherein a nanochannel is formed between said drain and said source.

14. The method for fabricating protein molecular junctions according to claim 13, wherein current regulation and charge transport of said drain and said source are controlled via applying said bias to said gate.

15. The method for fabricating protein molecular junctions according to claim 13, wherein said nanochannel has a width of 5-15 nm.

16. The method for fabricating protein molecular junctions according to claim 13, wherein said gold nanoparticle has a diameter of 5 nm.

* * * * *